United States Patent
Yu et al.

(10) Patent No.: US 8,052,961 B2
(45) Date of Patent: Nov. 8, 2011

(54) HIGHLY FLUORINATED β-AMINO ACIDS AND METHODS OF MAKING AND USING SAME

(75) Inventors: Bruce (Yihua) Yu, Ellicott City, UT (US); Zhong-Xing Jiang, Dundalk, MD (US)

(73) Assignee: University of Utah Foundation, Salt Lake, UT (US)

( * ) Notice: Subject to any disclaimer, the term of this patent is extended or adjusted under 35 U.S.C. 154(b) by 391 days.

(21) Appl. No.: 12/439,320

(22) PCT Filed: Sep. 14, 2007

(86) PCT No.: PCT/US2007/078549
§ 371 (c)(1),
(2), (4) Date: Apr. 26, 2009

(87) PCT Pub. No.: WO2008/034093
PCT Pub. Date: Mar. 20, 2008

(65) Prior Publication Data
US 2009/0259020 A1    Oct. 15, 2009

Related U.S. Application Data

(60) Provisional application No. 60/844,783, filed on Sep. 15, 2006.

(51) Int. Cl.
 A61K 8/21 (2006.01)
 A61K 8/30 (2006.01)
 A61K 38/08 (2006.01)
 C12P 7/52 (2006.01)
(52) U.S. Cl. .......................... 424/52; 435/141; 514/21.8
(58) Field of Classification Search ........................ None
See application file for complete search history.

(56) References Cited

OTHER PUBLICATIONS

Fustero, 2002, Journal of Organic Chemistry, 67, 4667-4679.*
Renaud, 1968, Canadian Journal of Chemistry, 46, 385-390.*
Aguilera et al. Novel disaccharide inhibitors of human glioma cell division. J. Med. Chem. 1998,41,4599-4606.
Bilgicer et al. De novo design of defined helical bundles in membrane environments. Proc. Natl. Acad. Scis. USA 2004, 101: 15324-15329.
Bohm et al. Fluorine in medicinal chemistry. ChemBioChem. 2004, 5, 637-643.
Bolo et al. Brain pharmacokinetics and tissue distribution in vivo of fluvoxamine and fluoxetine by fluorine magnetic resonance spectroscopy. Neuropsychopharmacology 2000, 23, 428-438.
Christensen et al. Measurement of human brain dexfenfluramine concentration by 19F magnetic resonance spectroscopy. Brain. Res. 1999; 834, 1-5.
Cybulla et al. End-stage renal disease after treatment with 90Y-DOTATOC. Eur. J. Nucl. Med.28, 1552-1554,2001.
Dalvit et al. Reliable high-throughput functional screening with 3-FABS. Drug Discovery Today 2004, 9, 595-602.

Dasgupta et al. Lipophilization of Somatostatin Analog RC-160 Improves its Bioactivity and Stability Pharmaceut. Res. 1999, 16:1047-1053.
Dasgupta et al. N-Terminal Acylation of Somatostatin Analog with Long Chain Fatty Acids Enhances its Stability and Anti-Proliferative Activity in Human Breast Adenocarcinoma Cells. Biol. Pharm. Bull. 2002. 25:29-36.
Durand et al. Synthesis and preliminary biological evaluations of ionic and nonionic amphiphilic alpha-phenyl-N-tert-butylnitrone derivatives. J. Med. Chem. 2003, 46, 5230-5237.
Gariepy et al. Vectorial delivery of macromolecules into cells using peptide-based vehicles. Trends in Biotech. 2001, 19,21-28.
Gentry et al. The effect of halogenation on blood-brain barrier permeability of a novel peptide drug. Peptides. 1999, 20, 1229-1238.
Gerebtzoff et al. Chem. BioChem. Chembiochem. 2004. 5(5):676-84.
Gerig et al. Binding of 5-fluorol-tryptophan to human serum albumin. J. Am. Chem. Soc. 1980,102,4267-4268.
Hsieh et al. Long-acting angiotensin II inhibitors containing hexafluorovaline in position 8. J. Med. Chem. 1987,30,1097-1100.
Hunter et al. Comparison of monthly intramuscular injections of Sandostatin LAR with multiple subcutaneous injections of octreotide in the treatment of acromegaly; effects on growth hormone and other markers of growth hormone secretion. Clin. Endocrin. 1999, 50,245-251.
Jiang et al. Asymmetric synthesis of both enantiomers of anti-4,4,4-trifluorothreonine and 2-amino-4,4,4-trifluorobutanoic acid. J. Org. Chem.68,7544-7547,2003.
Jiang et al. Synthesis of the Four Stereoisomers of N-Fmoc-O-t-Bu-4,4,4-trifluorothreonine. Biopolymers. 2005. 80(4):527.

(Continued)

*Primary Examiner* — Cecilia J Tsang
*Assistant Examiner* — Satyanarayana Gudibande
(74) *Attorney, Agent, or Firm* — Ballard Spahr LLP

(57) ABSTRACT

Disclosed are compounds having the structure:

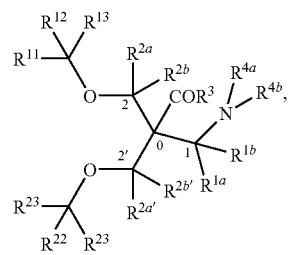

wherein $R^{1a}$ and $R^{1b}$ are independently H, alkyl, F, or fluoroalkyl; wherein $R^{2a}$, $R^{2b}$, $R^{2a'}$, and $R^{2b'}$ are independently H, alkyl, F, fluoroalkyl, aryl, or alkenyl; wherein $R^3$ is OH, alkoxyl, $NH_2$, alkylamino, or dialkylamino; wherein $R^{4a}$ and $R^{4b}$ are independently H, alkyl, acyl, or alkyloxycarbonyl; wherein $R_{11}$, $R_{12}$, $R_{13}$, $R_{21}$, $R_{22}$, and $R_{23}$ are independently H, alkyl, F, or fluoroalkyl; and wherein C0, C1, C2 and C2' are independently chiral or achiral. Also disclosed are processes for making a fluorinated β-amino acid comprising the steps of: providing a diol; treating the diol with a thionyl halide with oxidative workup; reacting the product with an azide salt to yield an azido group; oxidizing the product to yield a carboxyl group; and reducing the azido group to yield an amino group.

20 Claims, 3 Drawing Sheets

OTHER PUBLICATIONS

Jiang et al. The Synthesis of a Geminally Perfluoro-*tert*-butylated *â*-Amino Acid and its Protected Forms as a Potential Pharmacokinetic Modulator and Reporter for Peptide-Based Pharmaceuticals J. Org. Chem. 2007, 72, 1464-1467.

Kim et al. Structure and Transport Properties of a Novel, Heavily Fluorinated Carbohydrate Analogue. J. Am. Chem. Soc. 1998, 120:9082-9083.

Kommuru et al. Effect of chiral enhancers on the permeability of optically active and racemic metoprolol across hairless mouse skin. Chirality, I I, 536-540, 1999. 31.

Kovacs et al. Determination of intrinsic hydrophilicity/hydrophobicity of amino acid side chains in peptides in the absence of nearest-neighbor or conformational effects. Biopolymers, 2006, 84, 283-297.

Krause et al. Synthesis, X-ray crystallography, and pharmacokinetics of novel azomethine prodrugs of (R)-alpha-methylhistamine: highly potent and selective histamine H3 receptor agonists. J. Med. Chem. 1995,38,4070-4079.

Lien et al. Therapeutic Peptides. Trends in Biotech. 2003, 21, 556-562.

Merlo et al. Locoregional regulatory peptide receptor targeting with the diffusible somatostatin analogue 90Y-labeled DOTA0-D-Phe1-Tyr3-octreotide (DOTATOC): a pilot study in human gliomas. Clin. Cancer Res. 1999, 5,1025-1033.

Naarmann et al. Fluorinated interfaces drive self-association of transmembrane alpha helices in lipid bilayers. Chem. Int. Ed. 2006,45,2588-2591.

Neimz et al. Self-association and membrane-binding behavior of melittins containing trifluoroleucine. J. Am. Chem. Soc. 2001, 123, 7407-7413.

Ortial et al. Fluorinated amphiphilic amino acid derivatives as antioxidant carriers: a new class of protective agents. J. Med. Chem. 2006,49, 2812-2820.

Pardridge, W. Vector-mediated peptide delivery to the brain. M.Adv. Drug Del. Rev. 1995, 15, 109-146.

Park et al. Metabolism of fluorine-containing drugs. Ann. Rev. Pharmacol. Toxicol. 2001, 41, 443-470.

Reubi, J.C. Peptide receptors as molecular targets for cancer diagnosis and therapy. Endocrine Rev. 24, 389-427,2003.

Rubenstein et al. Hydrophilic, pro-drug analogues of T138067 are efficacious in controlling tumor growth in vivo and show a decreased ability to cross the blood brain barrier. J. Med. Chem. 2001,44, 3599-3605.

Rueter et al. Synthesis and biological activities of sandostatin analogs containing stereochemical changes in positions 6 or 8. Biopolymers, 53, 497-505,2000.

Schottelius et al. Modulation of pharmacokinetics of radioiodinated sugar-conjugated somatostatin analogs by variation of peptide net charge and carbohydration chemistry. Bioconj. Chem. 2005, 16(2), 429-437.

Schumacher et al. Local injection of the 90Y-labelled peptidic vector DOTATOC to control gliomas of WHO grades II and III: an extended pilot study. Eur J Nucl Med Mol Imaging. Apr. 2002;29(4):486-93.

Schweizer et al. A fluorine scan at the catalytic center of thrombin: C—F, C—OH, and C—OMe bioisosterism and fluorine effects on pKa and log D values. ChemMedChem, 2006, 6:611-621.

Sebesta et al. Facile Preparation of Perfluoro-tert-butyl Ethers by the Mitsunobu Reaction. J. Org. Chem. 1996, 61, 361-362.

Smith et al. OctreoTher: ongoing early clinical development of a somatostatin-receptor-targeted radionuclide antineoplastic therapy. Digestion, 62(Suppl 1) 69-72.2000.

Undevia et al. J. Pharmacokinetic Variability of Anticancer Agents. Nat. Rev. Cancer 2005,5, 447-458.

Wester et al. Comparison of radioiodinated TOC, TOCA and Mtr-TOCA: the effect of carbohydration on the pharmacokinetics. Eur. J. Nucl. Med. Mol. Imaging 2002, 29(1), 28-38.

Witt et al. CNS Drug Delivery: Opioid Peptides and the Blood-Brain Barrier. AAPS Journal. 2006; 8(1): E76-E88. DOI: 10.1208/aapsj080109.

Wulbrand et al. A novel somatostatin conjugate with a high affinity to all five somatostatin receptor subtypes. Cancer, 2002, 1293-1297.

Yu et al. Increasing fluorous partition coefficients by solvent tuning. Org. Lett. 2005, 7, 3677-3680.

Yu et al. Investigation of electrostatic interactions in two-stranded coiled-coils through residue shuffling. Biophys. Chem. 1996, 59: 299-314.

Yu et al. Ion pairs significantly stabilize coiled-coils in the absence of electrolyte. J. Mol. Biol. 1996,255, 367-372.

Zlokovic, B. V., Cerebrovascular permeability to peptides: manipulations of transport systems at the blood-brain barrier. Pharm. Res. 1995, 12, 1395-1406.

\* cited by examiner

HIGHLY FLUORINATED β-AMINO ACIDS AND METHODS OF MAKING AND USING SAME

CROSS REFERENCE TO RELATED APPLICATION

This application claims the benefit of priority of U.S. Provisional Application No. 60/844,783, filed Sep. 15, 2006, which application is incorporated herein by this reference in its entirety.

STATEMENT REGARDING FEDERALLY SPONSORED RESEARCH

This invention was made with government support under Grants Nos. NIH EB002880 and NIH EB004416 awarded by the National Institutes of Health. The government has certain rights in the invention.

Certain aspects of this work were supported with funding from the Sidney Kimmel Foundation for Cancer Research, wherein Yihua Yu was a Kimmel Scholar.

BACKGROUND

Peptides and their derivatives are becoming an increasingly important class of pharmaceuticals, both as drugs [Lien, S.; Lowman, H. B. Trends in Biotech. 2003, 21, 556-562.] and as drug delivery vehicles. [Gariepy, J.; Kawamura, K. Trends in Biotech. 2001, 19, 21-28.] Pharmacokinetics, defined as the in vivo absorption, distribution, metabolism, and excretion (ADME) profile of a drug, [Undevia, S. D.; Gomez-Abuin, G.; Ratain, M. J. Nat. Rev. Cancer 2005, 5, 447-458.] can be a factor in determining the efficacy and toxicity of peptide-based pharmaceuticals.

However, conventional peptide chemistry often fail to effectively provide avenues for the tailoring of pharmacokinetic characteristics of peptide-based pharmaceuticals. More specifically, conventional peptide synthesis methods typically fail to effectively provide routes to highly fluorinated β-amino acids. Further, delivery of drugs cross the blood-brain barrier (BBB) can be a very challenging issue. While fluorination has been used to enhance membrane permeability of other types of molecules, conventional peptide-based pharmaceuticals typically fail to effectively employ fluorinated moieties to enhance trans-BBB delivery. Moreover, conventional peptide-based pharmaceutical protocols typically lack effective non-invasive monitoring of drug pharmacokinetics, despite the much wider chemical shift range and much greater sensitivity of $^{19}F$ magnetic resonance spectroscopy ($^{19}F$ MRS). Thus, despite conventional peptide synthetic methodology, there remains a need for methods and compositions that overcome these deficiencies.

In contrast to conventional methods, the incorporation of fluorinated moieties can alter the pharmacokinetic characteristics, and thus the efficacy and toxicity, of peptide-based pharmaceuticals. Further, incorporation of fluorinated moieties can enhance trans-BBB delivery of peptide-based pharmaceuticals. Moreover, incorporation of fluorinated moieties can also provide functional groups that can serve as reporters of peptide pharmacokinetics via $^{19}F$ MRS.

SUMMARY

Disclosed are compounds having the structure:

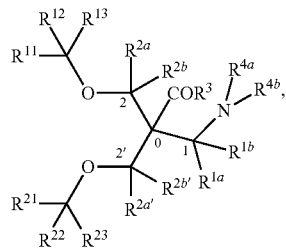

wherein $R^{1a}$ and $R^{1b}$ are independently H, alkyl, F, or fluoroalkyl; wherein $R^{2a}$, $R^{2b}$, $R^{2a'}$, and $R^{2b'}$ are independently H, alkyl, F, fluoroalkyl, aryl, or alkenyl; wherein $R^3$ is OH, alkoxyl, $NH_2$, alkylamino, or dialkylamino; wherein $R^{4a}$ and $R^{4b}$ are independently H, alkyl, acyl, or alkyloxycarbonyl; wherein $R_{11}$, $R_{12}$, $R_{13}$, $R_{21}$, $R_{22}$, and $R_{23}$ are independently H, alkyl, F, or fluoroalkyl; and wherein C0, C1, C2, and C2' are independently chiral or achiral.

Also disclosed are processes for making a fluorinated β-amino acid comprising the steps of: providing a diol having the structure:

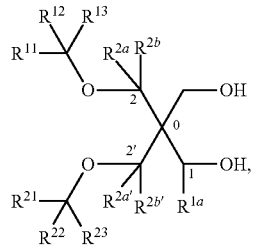

wherein $R^{1a}$ and $R^{1b}$ are independently H, alkyl, F, or fluoroalkyl; wherein $R^{2a}$, $R^{2b}$, $R^{2a'}$, $R^{2b'}$, $R^{11}$, $R^{12}$, $R^{13}$, $R^{21}$, $R^{22}$, and $R^{23}$ are independently H, alkyl, F, fluoroalkyl, aryl, or alkenyl; wherein $R^{11}$, $R^{12}$, $R^{13}$, $R^{21}$, $R^{22}$, and $R^{23}$ are independently F or fluoroalkyl; and wherein C0, C1, C2, and C2' are independently chiral or achiral; treating the diol with a thionyl halide with oxidative workup; reacting the product with an azide salt to yield an azido group; oxidizing the product to yield a carboxyl group; and reducing the azido group to yield an amino group.

Also disclosed are the products produced by the disclosed processes.

Also disclosed are pharmaceutical compositions comprising the disclosed compounds and products.

Also disclosed are peptides comprising at least one residue of a disclosed compound or at least one residue of a product of a disclosed process. For example, the disclosed peptides can have the structure:

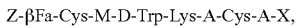

Z-βFa-Cys-M-D-Trp-Lys-A-Cys-A-X, wherein βFa comprises a residue of a disclosed compound or a residue of the product of a disclosed process; wherein each A independently comprises a residue of threonine or a residue of 4,4,4-trifluorothreonine; wherein M comprises Phe or Tyr or a derivative thereof; wherein X comprises a terminal end group selected from carboxyl, ester, amide, and alcohol; and wherein Z comprises a terminal end group selected from amino, formyl, acetyl, and succinyl.

Also disclosed are methods comprising the step of administering an effective amount of the disclosed compounds, products, compositions, and peptides.

Additional advantages can be set forth in part in the description which follows, and in part can be obvious from the description, or may be learned by practice. Other advantages can be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments and together with the description serve to explain the principles of the invention.

DETAILED DESCRIPTION

Figure 1:
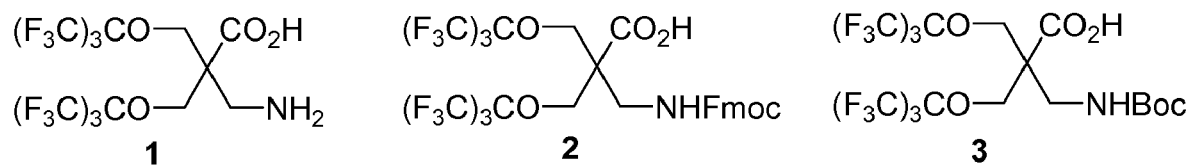
FIG. 1 shows the chemical structures of several disclosed highly fluorinated molecules (1, 2, and 3).

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

Although any methods and materials similar or equivalent to those described herein can be used in the practice or testing of the present invention, example methods and materials are now described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which may need to be independently confirmed.

As used in the specification and the appended claims, the singular forms "a," "an" and "the" include plural referents unless the context clearly dictates otherwise. Thus, for example, reference to "a compound," "a polymer," or "a particle" includes mixtures of two or more such compounds, polymers, or particles, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it can be understood that the particular value forms another embodiment. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "residue" refers to a moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 40 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkyloxycarbonyl" as used herein to refers to a group comprising the general structure:

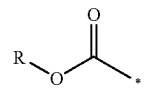

wherein R is an alkyl group, which can be substituted or unsubstituted. Examples of R substituents include t-butyl, benzyl, allyl, and 2,2,2-trichloroethyl. In one aspect, an alkyloxycarbonyl group can be used as a protecting group for an amine moiety. Examples of such protecting groups include Boc (tert-butyloxycarbonyl), Cbz (benzyloxycarbonyl), Alloc (allyloxycarbonyl), and Troc (2,2,2-trichloroethyloxycarbonyl).

The term "alkenyl" as used herein is a hydrocarbon group of from 2 to 40 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 40 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

As used herein, the term "fluorinated" refers to a compound or chemical moiety bearing at least one fluorine atom. That is, at least one hydrogen atom on a moiety has been instead substituted with at least one fluorine atom. One example is a trifluorinated ethyl group, —$CH_2CF_3$. By "perfluorinated," it is meant that all hydrogen atoms on a moiety have been instead substituted with fluorine atoms. One example is a perfluorinated methyl group, —$CF_3$.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

As used herein, the term "protecting group" refers to a chemical moiety that temporarily modifies a potentially reactive functional group and protects the functional group from undesired chemical transformations. Protecting group chemistry is known to one of skill in the art. See T. Greene, et al., "Protective Groups in Organic Synthesis," $2^{nd}$ ed., Wiley, N.Y., 1991, which is incorporated by reference herein for its teaching of protecting groups and methods of adding and removing protecting groups. Likewise, procedures for removal of the various protecting groups are known to those of skill in the art and are described in various references, including the above-listed "Protective Groups in Organic Synthesis."

Those of ordinary skill in the art appreciate that certain moieties are incompatible with (i.e., may interfere with) certain chemical transformations as described herein. Thus, it is understood that for certain chemical transformations, certain moieties, e.g., a hydroxyl group or an amino group (primary or secondary), are preferably protected by a suitable protecting group as described herein prior to those transformations. As used herein, the term "protected" refers to a chemical moiety that has been temporarily modified by a protecting group and has been thus protected from undesired chemical transformations. Upon removal of the protecting group (i.e., "deprotection"), the chemical moiety is typically liberated.

As used herein, the term "orthogonal," when used in connection with protecting groups, refers to the relationship between two or more protecting groups that have mutually exclusive deprotection reaction conditions. That is, one protecting group remains undisturbed under conditions that remove a second protecting group and vice versa. In one aspect, the two or more protecting groups are used to protect two or more chemical moieties having the same chemical structures (e.g., two or more amine moieties). In a further aspect, the two or more protecting groups are used to protect two or more chemical moieties having different chemical structures (e.g., an amine moiety and a carboxylic acid moiety). In a still further aspect, the two or more protecting groups are used to protect one or more chemical moieties having a first chemical structure and one or more chemical moieties having a second chemical structure (e.g., two amine moieties and one carboxylic acid moiety). An example of orthogonal protecting groups is the use of a tert-butyl (tBu) group to protect an alcohol and a 9-fluorenylmethyloxycarbonyl (Fmoc) group to protect an amine.

As used herein, the term "subject" means any target of administration. The subject can be an animal, for example, a mammal (e.g., a human, horse, pig, rabbit, dog, sheep, goat, non-human primate, cow, cat, guinea pig, or rodent), a fish, a bird or a reptile or an amphibian. The term does not denote a particular age or sex. Thus, adult and newborn subjects, as well as fetuses, whether male or female, are intended to be covered. In a further example, the subject can be a human. In an even further example, the subject can be a cell. A "patient" refers to a subject afflicted with a disease or disorder. The term "patient" includes human and veterinary subjects.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. In various aspects, a preparation can be administered therapeutically; that is, administered to treat an existing disease or condition. In further various aspects, a preparation can be administered diagnostically; that is, administered to diagnose an existing disease or condition. In further various aspects, a preparation can be administered prophylactically; that is, administered for prevention of a disease or condition. In a further aspect, "administering" and "administration" can refer to administration to cells that have been removed from a subject (e.g., human or animal), followed by re-administration of the cells to the same, or a different, subject.

As used herein, the term "effective amount" refers to such amount as is capable of performing the function of the compound or property for which an effective amount is expressed. As will be pointed out below, the exact amount required will vary from process to process, depending on recognized variables such as the compounds employed and the processing conditions observed. Thus, it is not typically possible to specify an exact "effective amount." However, an appropriate effective amount may be determined by one of ordinary skill in the art using only routine experimentation. In various aspects, an amount can be therapeutically effective; that is, effective to treat an existing disease or condition. In further various aspects, a preparation can be prophylactically effective; that is, effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents, and dispersing agents. Prevention of the action of microorganisms may be ensured by the inclusion of various antibacterial and antifungal agents such as paraben, chlorobutanol, phenol, sorbic acid, and the like. It can also be desirable to include isotonic agents such as sugars, sodium chloride, and the like. Prolonged absorption of the injectable pharmaceutical form may be brought about by the inclusion of agents, such as aluminum monostearate and gelatin, which delay absorption. Injectable depot forms can be made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Disclosed are the components to be used to prepare the compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. SYMBOLS AND ABBREVIATIONS

βFa: fluorinated beta-amino acid; Bn: benzyl; Boc: t-butoxycarbonyl; Bz: benzoyl; Cys: cysteine; DCC: 1,3-dicyclohexylcarbodiimide; DEAD: diethylazodicarboxylate; DMAP: 4-dimethylaminopyridine; Fmoc: fluorenylmethoxycarbonyl; HPLC: high-performance liquid chromatography; LC: liquid chromatography; Lys (K): lysine; MRI: magnetic resonance imaging; MRS: magnetic resonance spectroscopy; MS: mass spectrometry; Ms: methanesulfonyl; NMR: nuclear magnetic resonance; Phe: phenylalanine; tBu: t-butyl; TFA: trifluoroacetic acid; tfT: 4,4,4-trifluorothreonine; THF: tetrahydrofuran; Thr: threonine: Trp: tryptophan; and Tyr: tyrosine.

C. FLUORINATED β-AMINO ACIDS

As reported in "The Synthesis of a Geminally Perfluoro-tert-butylated β-Amino Acids and its Protected Forms as a Potential Pharmacokinetic Modulator and Reporter for Peptide-Based Pharmaceuticals" (Jian, Z.-X. and Yu, Y. B.; J. ORG. CHEM. 2007, 72, 1464-1467.), which is incorporated herein by reference in its entirety, the present invention addresses the aforementioned deficiencies in conventional peptide synthetic methodology.

From chemical synthesis standpoint, fluorinated amino acids are amenable to precise systematic variation (hence advantageous over polymer-based pharmacokinetic modulators [(a). Na, D. H.; Lee, K. C.; DeLuca, P. P. Pharm. Res. 2005, 22, 743-749. (b). Hunter, S. J.; Shaw, J. A.; Lee, K. O.; Wood, P. J.; Atkinson, A. B.; Bevan, J. S. Clin. Endocrin. 1999, 50, 245-251. (c). Wiit, K. A.; Davis, T. P. AAPS J. 2006, 8, E76-E88.]) and can be incorporated in a straightforward manner into any point of a peptide (hence advantageous over lipid-[Wiit, K. A.; Davis, T. P. AAPS J. 2006, 8, E76-E88.; (a). Dasgupta, P.; Singh, A. T.; Mukherjee, R. Pharmaceut. Res. 1999, 16, 1047-1053. (b). Dasgupta, P.; Singh, A.; Mukherjee, R. Biol. Pharm. Bull. 2002, 25, 29-36.] or sugar-[Wiit, K. A.; Davis, T. P. AAPS J. 2006, 8, E76-E88.; (a). Albert, R.; Marbach, P.; Bauer, W.; Briner, U.; Fricker, G.; Bruns, C.; Pless, J. Life. Sci. 1993, 53, 517-525. (b). Wester, H.-J.; Schottelius, M.; Scheidhauer, K.; Reubi, J.-C.; Wolf, I.; Schwaiger, M. Eur. J. Nucl. Med. 2002, 29, 28-38. (c). Schottelius, M.; Rau, F.; Reubi, J. C.; Schwaiger, M.; Wester, H.-J. Bioconjugate Chem. 2005, 16, 429-437.] based pharmacokinetic modulators).

Fluorination of a small peptide can enhance its membrane permeability and prolong its in vivo half-life, similar to effect of halogenation on BBB permeability and in vivo stability of opioid peptides. [Gentry, C. L.; Egleton, R. D.; Gillespie, T.; Abbruscato, T. J.; Bechowski, H. B.; Hruby, V. J.; Davis, T. P. Peptides, 1999, 20, 1229-1238.; Abbruscato, T.; Williams, S.; Misicka, A.; Lipkowski, A. W.; Hruby, V. J.; Davis, T. P. J. Pharmacol. Exp. Therapeut. 1996, 276, 1049-1057.] Due to low BBB permeability, octreotide-based pharmaceuticals are currently injected into a patient's brain using a stereotactically inserted port-a-cath. [(a). Merlo, A.; hausmann, O.; Wasner, M.; Steiner, P.; Otte, A.; Jermann, E.; Freitag, P.; Reubi, J.-C.; Muller-Brand, J.; gratzl, O.; Macke, H. R. Clin. Cancer Res. 1999, 5, 1025-1033. (b). Schumacher, T.; Hofer, S.; Eichhorn, K.; Wasner, M.; Zimmerer, S.; Freitag, P.; Probst, A.; Gratzl, O.; Reubi, J.-C.; Maecke, H. R.; Mueller-Brand, J.; Merlo, A. Eur. J. Nucl. Med. 2002, 29, 486-493.] Non-invasive delivery across BBB is highly desirable.

Two exemplary classes of fluorinated amino acids are designed and synthesized. The first class of fluorinated amino acids can be incorporated outside the receptor-binding site of peptide pharmaceuticals (most likely conjugated to the N-, C-termini of a peptide). This class of amino acids does not need to take the specifics of each peptide pharmaceutical into consideration and does not have to resemble natural amino acids. They can serve as a generic tag for pharmacokinetic modulation and $^{19}$F-MRS detection. The second class of fluorinated amino acids can be incorporated into the receptor-binding site of a peptide pharmaceutical. This class of amino acids takes into account the specifics of each peptide pharmaceutical and, thus, can closely resemble the original amino acids in the peptide pharmaceutical.

Mindful of the possibility that fluorination can, in some cases, decrease the hydrophobicity of a molecule [(a). Böhm, H.-J.; Banner, D.; Bendels, S.; Kansy, M.; Kuhn, B.; Müller, K.; Obst-Sander, U.; Stahl, M. Chem Bio Chem. 2004, 5, 637-643. (b). Schweizer, E.; Hoffmann-Röder, A.; Schärer, K.; Olsen, J. A.; Fäh, C.; Seiler, P.; Obst-Sander, U.; Wagner, B.; Kansy, M.; Diederich, F. Chem Med Chem, 2006, 1, 611-621.] and hence reduce membrane permeability, [Abbruscato, T.; Williams, S.; Misicka, A.; Lipkowski, A. W.; Hruby, V. J.; Davis, T. P. J. Pharmacol. Exp. Therapeut. 1996, 276, 1049-1057.] the hydrophobicity and 1-octanol/water partition coefficient ($P_{oct}$) of βFa are determined in the context of a tripeptide. Note that $P_{oct}$ is a standard physicochemical parameter in assessing BBB permeability of peptides and other drugs. [Gentry, C. L.; Egleton, R. D.; Gillespie, T.; Abbruscato, T. J.; Bechowski, H. B.; Hruby, V. J.; Davis, T. P. Peptides, 1999, 20, 1229-1238.; Abbruscato, T.; Williams, S.; Misicka, A.; Lipkowski, A. W.; Hruby, V. J.; Davis, T. P. J. Pharmacol. Exp. Therapeut. 1996, 276, 1049-1057.]

D. DESIGN OF AMINO ACID AND MODEL TRIPEPTIDE

A generic tag fluorinated amino acid typically has the following attributes. For membrane permeation: high hydrophobicity. For $^{19}$F-MRS detection: $^{19}$F NMR signal is a strong singlet. For peptide incorporation: Fomc- and Boc-protected forms can be readily prepared with high yield and purity. The fluorinated amino acid 1 as depicted in FIG. 1, along with its Fmoc- and Boc-protected forms (2 and 3, respectively), was designed and prepared.

This amino acid 1 is highly fluorinated (fluorine content is 58.4%) and hence effectively promotes hydrophobicity. The fluorine atoms are introduced into the amino acid through two symmetrically positioned perfluoro-tert-butyl groups. This ensures that all of the 18 fluorine atoms have identical chemical environment and avoids $^{19}$F-$^{19}$F or $^{19}$F-$^{1}$H coupling. As a result, this amino acid to gives a single $^{19}$F NMR signal. This amino acid is achiral due to the symmetric arrangement of the perfluoro-tert-butyl groups. The inertness of the perfluoro-tert-butyl group makes side chain protection unnecessary. Achirality and side chain inertness significantly simplify the synthesis of both the free amino acid and its protected forms. Considering that electron-withdrawing capacity of perfluoro-tert-butyl groups typically weakens the basicity of the amino group while strengthening the acidity of the carboxylic group, a β-amino acid is adopted to ensure sufficient separation between the amino group and the two perfluoro-tert-butyl groups. This also allows better steric accommodation of the relatively bulky perfluoro-tert-butyl groups.

Figure 2:
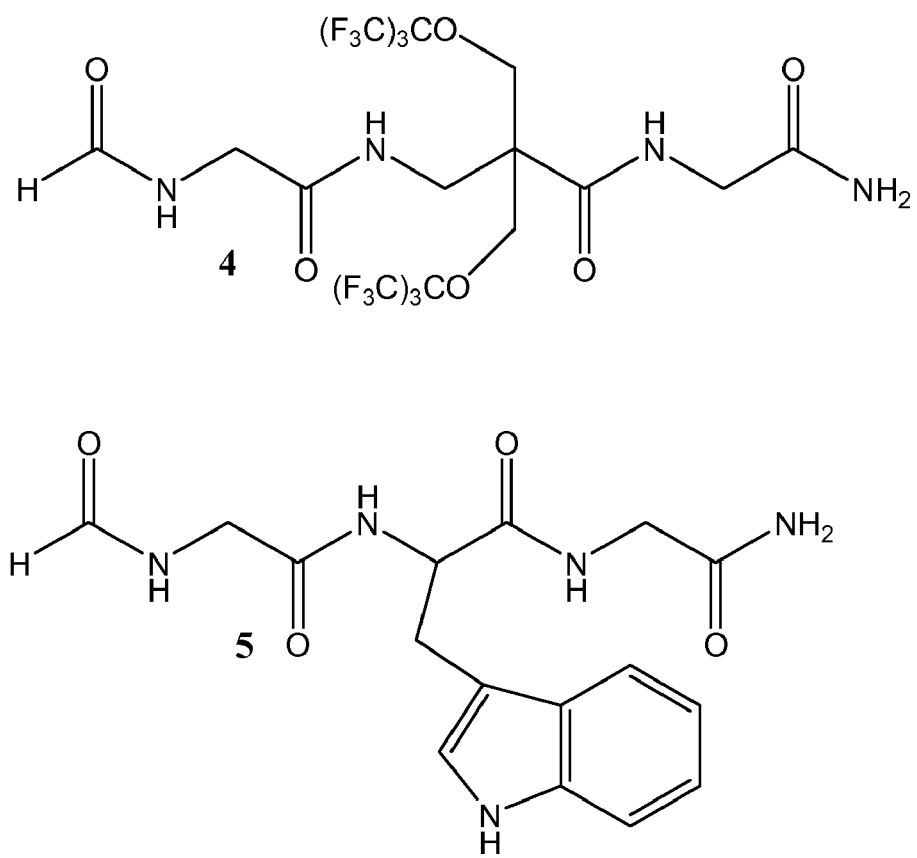
FIG. 2 shows the chemical structures of two tripeptides: formyl-Gly-βFa-Gly-amide (4) and formyl-Gly-Trp-Gly-amide (5).

To demonstrate the feasibility of fluorinated β-amino acids (βFa) to be incorporated into peptides via solid-phase synthesis, the following tripeptide formyl-Gly-βFa-Gly-amide 4 was designed. In one aspect, βFa is positioned in the middle of the tripeptide to demonstrate that βFa can be placed in any position of a peptide, not just the N-, C-terminals. In one aspect, the N- and C-termini of the tripeptide are formylated and amidated, respectively. These modifications abolish terminal charges of the tripeptide so that they will not interfere with hydrophobicity and octanol/water partition measurements. Note that the disentanglement of hydrophobic interactions from electrostatic interections in peptides/proteins can be far from trivial. [(a). Yu, Y.; Monera, O. D.; Hodges, R. S.; Privalov, P. L. J. Mol. Biol. 1996, 255, 367-372. (b). Yu, Y.; Monera, O. D.; Hodges, R. S.; Privalov, P. L. Biophys. Chem. 1996, 59, 299-314.] In this example, two glycine residues, which have no side chains, flank the central βFa. The purpose is to abolish nearest neighbor interactions, which can also interfere with hydrophobicity measurements. [Kovacs, J. M.; Mant, C. T.; Hodges, R. S. Biopolymers, 2006, 84, 283-297.] Hence, this tripeptide provides a "clean" model system for hydrophobicity and 1-octanol/water partition measurements. A reference tripeptide 5 contains tryptophan (Trp) in place of βFa. Trp is the most hydrophobic one among the 20 natural amino acids [Kovacs, J. M.; Mant, C. T.; Hodges, R. S. Biopolymers, 2006, 84, 283-297.] and is as an excellent reference for hydrophobicity measurements. Structures of the two example tripeptides (4 and 5) are shown in FIG. 2.

E. COMPOUNDS

In one aspect, the invention relates to a compound having the structure:

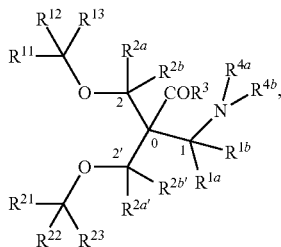

wherein $R^{1a}$ and $R^{1b}$ are independently H, alkyl, F, or fluoroalkyl; wherein $R^{2a}$, $R^{2b}$, $R^{2a'}$, and $R^{2b'}$ are independently H, alkyl, F, fluoroalkyl, aryl, or alkenyl; wherein $R^3$ is OH, alkoxyl, $NH_2$, alkylamino, or dialkylamino; wherein $R^{4a}$ and $R^{4b}$ are independently H, alkyl, acyl, or alkyloxycarbonyl; wherein $R_{11}$, $R_{12}$, $R_{13}$, $R_{21}$, $R_{22}$, and $R_{23}$ are independently H, alkyl, F, or fluoroalkyl; and wherein C0, C1, C2, and C2' are independently chiral or achiral. In a further aspect, $R^{11}=R^{12}=R^{13}$. In a still further aspect, $R^{21}=R^{22}=R^{23}$. In a yet further aspect, $R^{11}$, $R^{12}$, $R^{13}$, $R^{21}$, $R^{22}$, and $R^{23}$ are fluoroalkyl. In a further aspect, $R^{11}$, $R^{12}$, $R^{13}$, $R^{21}$, $R^{22}$, and $R^{23}$ are $CF_3$.

In one aspect, the invention relates to a compound wherein $R^{1a}$, $R^{1b}$, $R^{2a}$, $R^{2b}$, $R^{2a'}$, and $R^{2b'}$ are H; wherein C1, C2, and C2' are achiral; and wherein the compound has the structure:

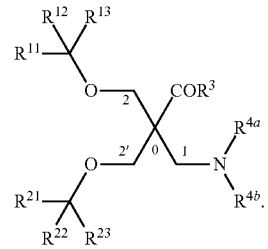

In a further aspect, $R^{11}=R^{12}=R^{13}=R^{21}=R^{22}=R^{23}$ and C0 is achiral. In a further aspect, $R^{11}=R^{12}=R^{13}\neq R^{21}=R^{22}=R^{23}$ and wherein C0 is chiral. In a further aspect, $R^{11}$, $R^{12}$, $R^{13}$, $R^{21}$, $R^{22}$, and $R^{23}$ are $CF_3$; $R^{4a}$ is H; $R^{4b}$ is H or Fmoc; and the compound has the structure:

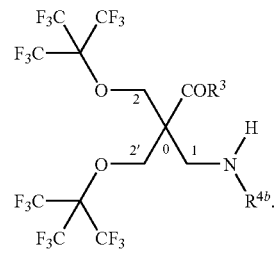

In a further aspect, $R^{4a}$ or $R^{4b}$ is H. In a further aspect, $R^{4a}$ or $R^{4b}$ is alkyloxycarbonyl. In a further aspect, $R^{4a}$ or $R^{4b}$ is nBoc, tBoc, or Fmoc. In a further aspect, $vR^{4a}$ or $R^{4b}$ is peptide; that is, in certain aspects, a compound can be incorporated within a peptide.

In certain aspects, $R^3$ is OH. In a further aspect, $R^3$ is methoxyl, ethoxyl, propoxyl, butoxyl, benzyloxyl, or phenoxyl. In a still further aspect, $R^3$ is peptide.

It is also understood that the compounds can be provided as a carboxylic acid or a salt thereof or a carboxylate derivative thereof. That is, in one aspect, the carboxylic acid moiety can be optionally provided as a salt thereof. Suitable salts include monovalent, divalent, and trivalent salts. Monovalent salts include salts prepared with monovalent cations, including ammonium salts, quaternary amine salts, lithium salts, sodium salts, potassium salts, and the like. Divalent salts include salts prepared with divalent cations, including beryllium salts, magnesium salts, calcium salts, and the like. Trivalent salts include salts prepared with trivalent cations, including aluminum salts, iron salts, Ln(III) salts, and the like. It is also understood that, in one aspect, the carboxylic acid moiety can be optionally provided as a carboxylate derivative (i.e., a protected carboxylate) thereof. Suitable carboxylate protecting groups include, but are not limited to, esters, including substituted or unsubstituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, tert-butyl, benzyl, and phenyl wherein each group is optionally substituted. Said another way, in one aspect, the carboxylic acid structure is intended to include salts thereof and derivatives thereof, as disclosed herein, as well as equivalents thereof.

F. METHODS OF MAKING

1. Synthesis of an Exemplary Amino Acid

The commercially available pentaerythritol provides an ideal starting material for the synthesis of compound 1. An exemplary synthesis commenced with the selective protection of pentaerythritol 6 (SCHEME 1). Protecting two of the four hydroxyl groups in pentaerythritol 6 with p-methoxy] benzaldehyde gave the alcohol 7 with good yield. [Aguilera, B.; Romero-Ramirez, L.; Abad-Rodriguez, J.; Corrales, G.; Nieto-Sampedro, M.; Fernandez-Mayoralas, A. J. Med. Chem. 1998, 41, 4599-4606.] As the acidity of the hydroxyl group in perfluoro-tert-butanol is enhanced by the three electron-withdrawing —$CF_3$ groups, perfluoro-tert-butanol is a good substrate for the Mitsunobu reaction to form perfluoro-tert-butyl ethers. [Sebesta, D. P.; O'Rourke, S. S.; Pieken, W., A. J. Org. Chem. 1996, 61, 361-362.] Thus, the Mitsunobu reaction was employed to introduce two perfluoro-tert-butyl groups into compound 7 in just one step to give fluorinated ether 8 with 98% yield after the reaction mixture was stirred at 45° C. for 30 hours. Such a high yield can be achieved, for example, by carrying out the reaction in a sealed vessel and in the presence of 4 Å molecular sieve. With a fluorine content of 49.5%, the fluorinated ether 8 can be extracted from the reaction mixture with fluorous solvents. [Yu, M. S.; Curran, D. P.; Nagashima, T. Org. Lett. 2005, 7, 3677-3680.]; however, FC-72 ($C_6F_{14}$) nor HFE-7100 (a mixture of n-$C_4F_9OCH_3$ and i-$C_4F_9OCH_3$) were not ideal solvents for the extraction of compound 8 from the acetonitrile/water (95%/5%) solution of the reaction mixture. As an alternative to extraction, standard flash chromatography can be used to purify ether 8 with a 98% yield. The p-methoxybenzylidene acetal protection group was cleaved from compound 8 by powdered aluminum chloride in the presence of anisole to give 1,3-diol 9 with quantitative yield. Treatment of 1,3-diol 9 with thionyl chloride gave a cyclic sulfite intermediate which can then be oxidized by in situ generated ruthenium tetraoxide to give the cyclic sulfate 10 with an 84% yield in two steps. Ring opening of the cyclic sulfate 10 with sodium azide, followed by hydrolysis of the resulting sulfonic acid, gave the azido compound 11 with excellent yield which can then be subjected to Jones oxidation to give the carboxylic acid 12 with an 85% yield. Hydrogenation of the azido group in compound 12 yielded the fluorinated amino acid 1 with excellent yield.

SCHEME 1: Synthesis of 1

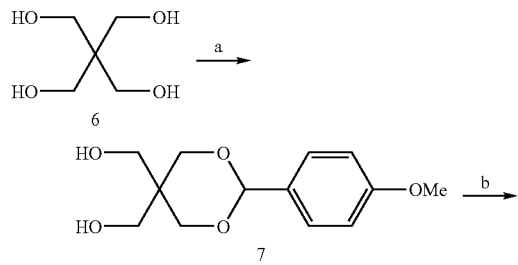

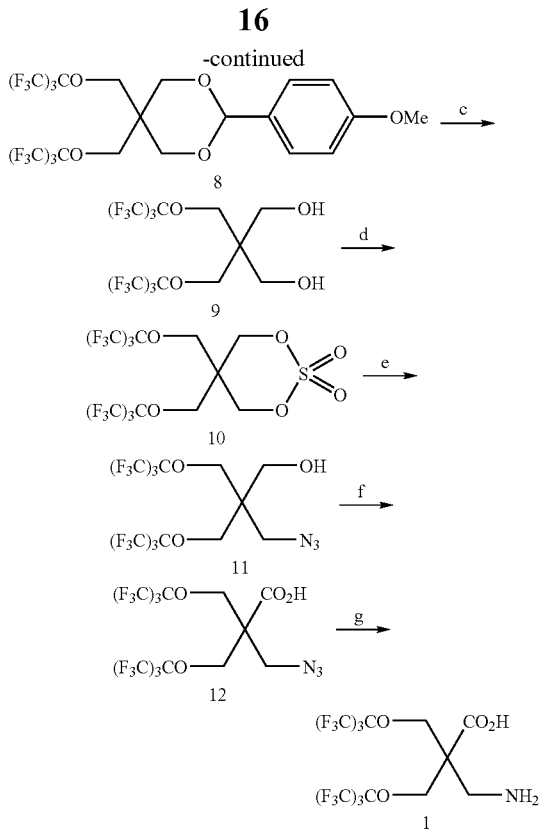

Reagents and conditions:
a. p-anisaldehyde, HCl (aq.), $H_2O$, rt. 87%;
b. DEAD, $Ph_3P$, 4Å MS, $(CF_3)_3COH$, THF, 45° C., 98%
c. $AlCl_3$, PhOMe, $CH_2Cl_2$, rt. 99%;
d. (1). $SOCl_2$, $Et_3N$, $CH_2Cl_2$—$Et_2O$, rt.;
(2). $NaIO_4$, $RuCl_3$, $H_2O$—$CH_3CN$—$CCl_4$ (3:2:2), rt. 85% for 2 steps;
e. (1). $NaN_3$, DMF, 60° C.; (2). $H_2SO_4$, $H_2O$, THF, rt. 97% for 2 steps;
f. Jones reagent, Acetone, rt. 95%;
g. $H_2$, Pd/C, MeOH, rt. 98%.

2. Synthesis of Fmoc- and Boc-Protected Forms of the Amino Acid

To obtain the Fmoc-protected form of the amino acid, the amino group of compound 1 can be reacted with 9-fluorenylmethoxycarbonyl chloride (FmocCl) to give compound 2 with a 96% yield on a 13.3-gram scale, as depicted in SCHEME 2.

SCHEME 2: Synthesis of 2

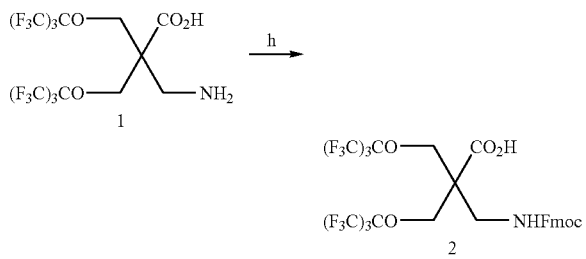

Reagents and conditions:
h. FmocCl, $Na_2CO_3$, THF-$H_2O$ (1:1), rt. 96%.

To obtain the Boc-protected form of the amino acid, the azido group of compound 12 can be reduced to the amino group which then can be reacted with di-tert-butyl dicarbonate ($Boc_2O$) to give compound 3 with a 96% yield on a 1.3-gram scale, as depicted in SCHEME 3.

SCHEME 3: Synthesis of 3

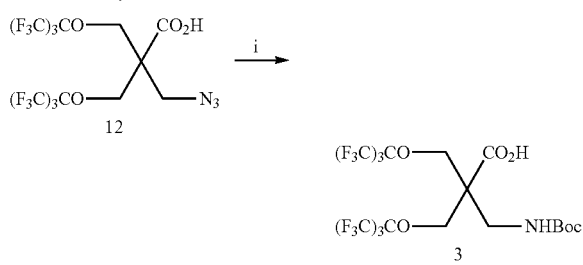

Reagents and conditions:
i. Boc$_2$O, H$_2$, Pd/C, MeOH, rt. 96%.

3. Synthesis of βFa Containing Tripeptide 4 and Reference Peptide 5

The two tripeptides can be synthesized using standard Fmoc chemistry on a solid support. [Chan, W. C.; White, P. D. Fmoc Solid Phase Peptide Synthesis: A Practical Approach; Oxford University Press: New York: 2000; pp 1-75.] βFa showed good reactivity at both the carboxyl group and the amino group. Hence, βFa can be incorporated into any position of a target peptide through its carboxyl group, amino group, or both. Formyl-Gly-βFa-Gly-amide 4 can be purified by normal-phase HPLC, while formyl-Gly-Trp-Gly-amide 5 can be purified by reversed-phase HPLC. The molecular mass and the purity of each tripeptide were verified by mass spectrometry and analytical HPLC, respectively.

4. $^{19}$F NMR Characterization

Figure 3:
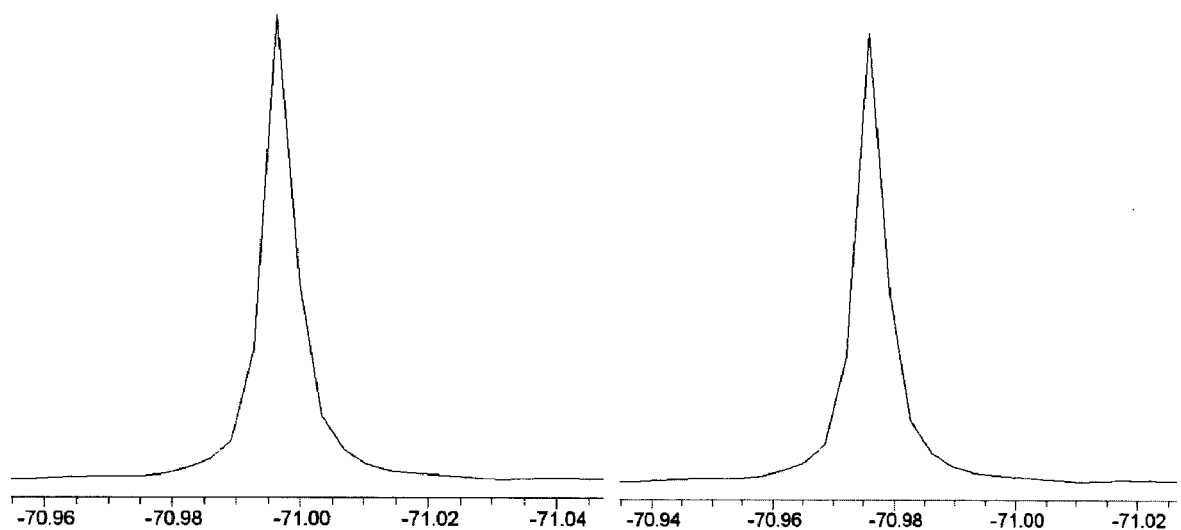
FIG. 3 shows the chemical shift (ppm) of $^{19}$F NMR in free amino acid 1 (left) and tripeptide 4 (right) (376 MHz, $CD_3OD$, $C_6F_6$ as internal standard).

The $^{19}$F NMR spectra of the free amino acid 1 and Formyl-Gly-βFa-Gly-amide 4 are shown in FIG. 3. As designed, all 18 fluorine atoms give a single sharp $^{19}$F signal (line width ~0.01 ppm) in both the free amino acid 1 (left) and the tripeptide 4 (right). This is also the case for the two protected forms (compound 2 and 3) of this amino acid.

5. Processes

In one aspect, the invention relates to a process for making a fluorinated β-amino acid comprising the steps of: providing a diol having the structure:

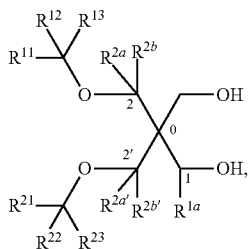

wherein R$^{1a}$ and R$^{1b}$ are independently H, alkyl, F, or fluoroalkyl; wherein R$^{2a}$, R$^{2b}$, R$^{2a'}$, R$^{2b'}$, R$^{11}$, R$^{12}$, R$^{13}$, R$^{21}$, R$^{22}$, and R$^{23}$ are independently H, alkyl, F, fluoroalkyl, aryl, or alkenyl; wherein R$^{11}$, R$^{12}$, R$^{13}$, R$^{21}$, R$^{22}$, and R$^{23}$ are independently F or fluoroalkyl; and wherein C0, C1, C2, and C2' are independently chiral or achiral; treating the diol with a thionyl halide with oxidative workup; reacting the product with an azide salt to yield an azido group; oxidizing the product to yield a carboxyl group; and reducing the azido group to yield an amino group. In a further aspect, the reducing step is performed before the oxidizing step.

In a further aspect, R$^{1a}$, R$^{2a}$, R$^{2b}$, R$^{2a'}$, and R$^{2b'}$ are H; R$^{11}$, R$^{12}$, R$^{13}$, R$^{21}$, R$^{22}$, and R$^{23}$ are CF$_3$; and the compound has the structure:

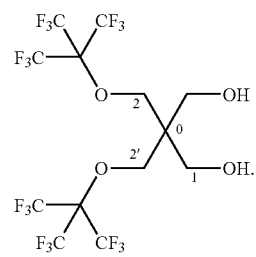

In a further aspect, the product of the treating step has the structure:

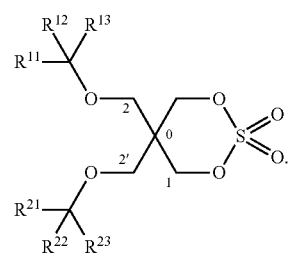

In one aspect, the providing step comprises the steps of: providing a tetra-ol; and protecting two hydroxyl groups of the tetra-ol. In a further aspect, the protecting step is reaction with a carbonyl compound to form a cyclic ketal or cyclic acetal. In a further aspect, the carbonyl compound is p-anisaldehyde.

G. COMPOSITIONS

In one aspect, the invention relates to a peptide comprising at least one residue of a disclosed compound or at least one residue of the product of a disclosed process. For example, the invention relates to a pharmaceutical composition comprising a therapeutically effective amount of one or more compounds comprising the product of a disclosed process, or a residue thereof, or a disclosed compound, or a residue thereof, or a disclosed peptide, or a residue thereof, and a pharmaceutically acceptable carrier for administration in a mammal.

In a further aspect, the invention relates to a peptide having the structure:

Z-βFa-Cys-M-D-Trp-Lys-A-Cys-A-X, wherein βFa comprises a residue of a disclosed compound or a residue of the product of a disclosed process; wherein each A independently comprises a residue of threonine or a residue of 4,4,4-trifluorothreonine; wherein M comprises Phe or Tyr or a derivative thereof (i.e., a substituted Phe or Tyr, for example, iodinated Tyr or nitrated Tyr); wherein X comprises a terminal end group selected from carboxyl, ester, amide, and alcohol; and wherein Z comprises a terminal end group selected from amino, formyl, acetyl, and succinyl. In a still further aspect, the cysteine residues are linked by a disulfide bond.

In a further aspect, the peptide has the structure:

Z-βFa-Cys-M-D-Trp-Lys-A-Cys-tfT-X, wherein each A independently comprises a residue of threonine or a residue of 4,4,4-trifluorothreonine; and wherein tfT comprises a residue of 4,4,4-trifluorothreonine.

In a further aspect, the peptide has the structure:

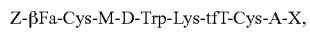

wherein each A independently comprises a residue of threonine or a residue of 4,4,4-trifluorothreonine; and wherein tfT comprises a residue of 4,4,4-trifluorothreonine.

In a further aspect, the peptide has the structure:

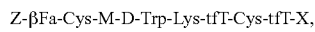

wherein tfT comprises a residue of 4,4,4-trifluorothreonine.

H. METHODS OF USING

In certain aspects, the invention relates to the use of the disclosed compounds and compositions to modulate peptide properties (e.g., enhance membrane permeability, enhance in vivo half-life, and/or enhance detection in peptide-based pharmaceuticals) by the incorporation of fluorinated moieties.

1. Modulation of Peptide Properties
   a. Enhanced Membrane Permeability

Increasing membrane permeability of peptide drugs so that they can cross the blood-brain barrier (BBB), can be a very challenging issue in drug delivery. [(a). Zlokovic, B. V. *Pharm. Res.* 1995, 12, 1395-1406. (b). Pardridge, W. M. *Adv. Drug Del. Rev.* 1995, 15, 109-146.] Although fluorination has been reported to drive the self-association of transmembrane α-helices [(a). Bilgiçer, B.; Kumar, K. *Proc. Natl. Acad. Scis. USA* 2004, 101, 15324-15329. (b). Naarmann, N.; Bilgiçer, B.; Meng, H.; Kumar, K.; Steinem, C. *Angew. Chem. Int. Ed.* 2006, 45, 2588-2591.] and membrane binding proteins [Neimz, A.; Tirrell, D. A. *J. Am. Chem. Soc.* 2001, 123, 7407-7413.] in lipid bilayers, it is well-established that fluorination can enhance membrane permeability of other types of molecules. For example, many drugs with high membrane permeability, such as psychotropic agents (e.g., fluoxetine, fluvaxamine and fluphenazine) and inhalation anesthetics (e.g., desflurane, isoflurane, sevoflurane), contain the trifluoromethyl group (—$CF_3$) attached to either aromatic carbons or aliphatic carbons. Fluorination can also enhance membrane permeability of other drugs, such as antioxidants. [(a). Durand, G.; Polidori, A.; Ouari, O.; Geromel, V.; Rustin, P.; Pucci, B. *J. Med. Chem.* 2003, 46, 5230-5237; (b). Ortial, S.; Durand, G.; Poeggeler, B.; Polidori, A.; Pappolla, M. A.; Böker, J.; Hardeland, R.; Pucci, B. *J. Med. Chem.* 2006, 49, 2812-2820.] In contrast, defluorination can lead to decreased membrane permeability. [Rubenstein, S. M.; Baichwal, V.; Beckmann, H.; Clark, D. L.; Frankmoelle, W.; Roche, D.; Santha, E.; Schwender, S.; Thoolen, M.; Ye, Q.; Jaen, J. C. *J. Med. Chem.* 2001, 44, 3599-3605.] Although detailed mechanisms are not entirely clear from membrane biophysics standpoint, it is generally accepted that enhanced membrane permeability is caused by enhanced hydrophobicity brought by fluorination. [(a). Krause, M.; Rouleau, A.; Stark, H.; Luger, P.; Lipp, R.; Garbarg, M.; Schwartz, J.-C.; Schunack, W. *J. Med. Chem.* 1995, 38, 4070-4079. (b). Park, B. K.; Kitteringham, N. R.; O'Neill, P. M. *Ann. Rev. Pharmacol. Toxicol.* 2001, 41, 443-470. (c). Gerebtzoff, G.; Li-Blatter, X.; Fischer, H.; Frentzel, A.; Seelig, A. *Chem Bio Chem* 2004, 5, 676-684.] For example, it was found that there is a correlation between BBB permeability and hydrophobicity of halogenated opioid peptides. [Gentry, C. L.; Egleton, R. D.; Gillespie, T.; Abbruscato, T. J.; Bechowski, H. B.; Hruby, V. J.; Davis, T. P. *Peptides,* 1999, 20, 1229-1238.]

b. Enhanced In Vivo Half-Life

Other than membrane permeability, we are also interested in prolonging the in vivo half-life ($t_{1/2}$) of peptide drugs. $t_{1/2}$ is a critical factor in determining the therapeutic efficacy of peptide drugs. For example, it took fifteen years to convert the natural tetradeca-peptide hormone somatostatin into an approved octapeptide drug octreotide (Sandostatin®), primarily to prolong the $t_{1/2}$ of somatostatin (from 2 minutes to 2 hours). [Marbach, P.; Briner, U.; Lemaire, M.; Schweitzer, A.; Terasaki, T. *Metabolism,* 1992, 41 (Suppl. 2), 7-10.] Further prolonging the in vivo $t_{1/2}$ of octreotide is an on-going research topic. [Wulbrand, U.; Feldman, M.; Pfestroff, A.; Fehman, H.-C.; Du, J.; Hiltunen, J.; Marquez, M.; Arnold, R.; Westlin, J.-E.; Nilsson, S.; Holmberg, A. R. *Cancer,* 2002, 1293-1297.] In this regard, it is well known that introduction of fluorinated amino acids can prolong the in vivo half-life ($t_{1/2}$) of peptides. [Hsieh, K.-H.; Needleman, P.; Marshall, G. R. *J. Med. Chem.* 1987, 30, 1097-1100.]

c. Enhanced Detection

From a pharmacokinetic reporting standpoint, compared with $^1H$, $^{19}F$ has a comparable sensitivity (ca. 83% as sensitive), a much wider chemical shift range (ca. 20 times wider) and no detectable endogenous background signal. This makes $^{19}F$ ideally suited for non-invasive monitoring of drug pharmacokinetics via $^{19}F$ magnetic resonance spectroscopy ($^{19}F$ MRS). Of courses, our intention is to monitor the pharmacokinetics of the fluorinated peptide drug via $^{19}F$ MRS, rather than using $^{19}F$ MRS of a fluorinated drug to infer the pharmacokinetics of its non-fluorinated counterpart. The wide chemical shift range and high sensitivity of the $^{19}F$ nucleus allows $^{19}F$ MRS to detect both covalent and non-covalent changes occurring to a molecule. [(a). Gerig, J. T.; Klinkenborg, J. C.; *J. Am. Chem. Soc.* 1980, 102, 4267-4268. (b). Jenkins, B. G.; Lauffer, R. B. *Mol. Pharmacol.* 1990, 37, 111-118. (c). Dalvit, C.; Ardini, E.; Fogliatto, G. P.; Mongelli, N.; Veronesi, M. *Drug Discovery Today* 2004, 9, 595-602.] For example, $^{19}F$ MRS has been used to monitor the transport of fluorinated molecules across biological membranes, [(a). Xu, A. S. L., Waldeck, R.; Kuchel, P. W. *NMR in Biomedicine,* 1993, 6, 136-143. (b). Kim, H. W.; Rossi, P.; Shoemaker, R. K.; DiMagno, S. G. *J. Am. Chem. Soc.* 1998, 120, 9082-9083.] a feature well-suited of our future applications. In fact, $^{19}F$ MRS has already been used in clinical settings for pharmacokinetic monitoring. [(a). Renshaw, P. F.; Guimaraes, A. R.; Fava, M.; Rosenbaum, J. F.; Pearlman, J. D.; Flood, J. G.; Puopolo, P. R.; Clancy, K.; Gonzalez, R. G. *Am. J. Psychiatry* 1992, 149, 1592-1594. (b). Christensen, J. D.; Yurgelun-Todd, D. A.; Babb, S. M.; Gruber, S. A.; Cohen, B. M.; Renshaw, P. F. *Brain. Res.* 1999; 834, 1-5. (c). Bolo, N. R.; Hode, Y.; Nedelec, J.-F.; Laine, R.; Wagner, G.; Macher, J.-P. *Neuropsychopharmacology* 2000, 23, 428-438.]

2. Administration

In one aspect, the invention relates to a method comprising the step of administering an effective amount of one or more compounds comprising the product of a disclosed process, or a residue thereof, or a disclosed compound, or a residue thereof, or a disclosed peptide, or a residue thereof, to a subject. In a further aspect, the method further comprises the step of detecting fluorine. In a still further aspect, the detecting step is performed with $^{19}F$ NMR.

I. HYDROPHOBICITY MEASUREMENTS

Figure 4:
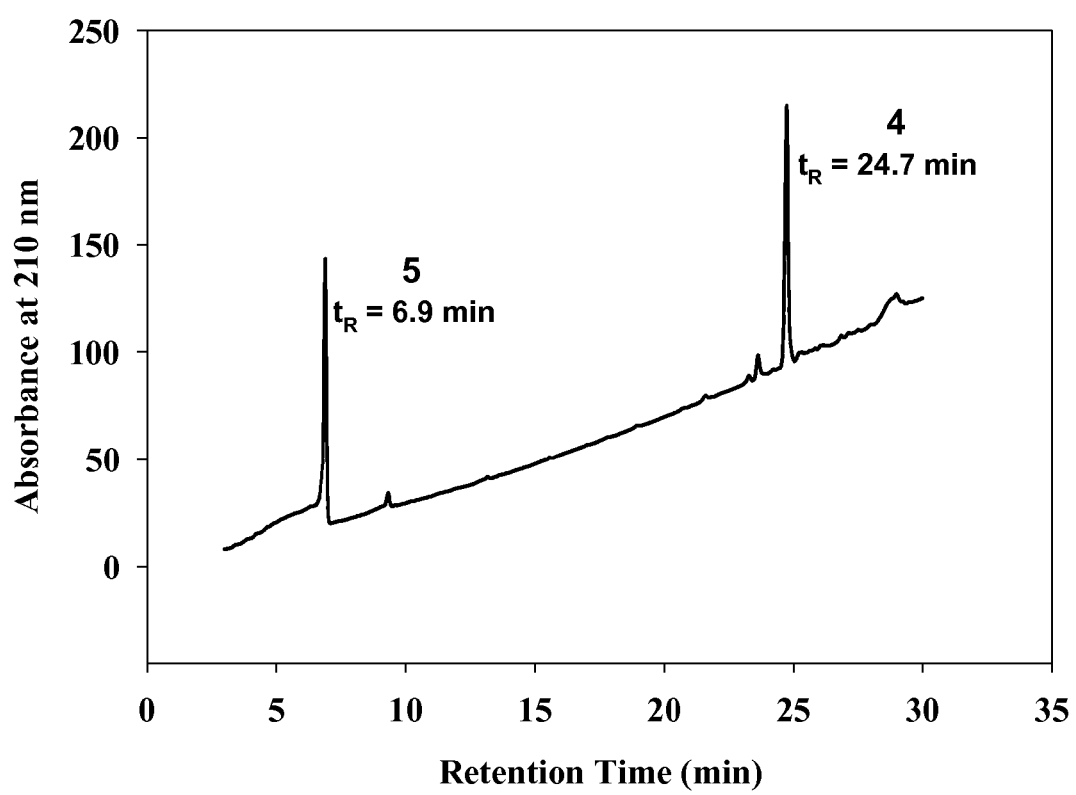
FIG. 4 shows the determination of hydrophobicity by RP-HPLC.
Figure 5:
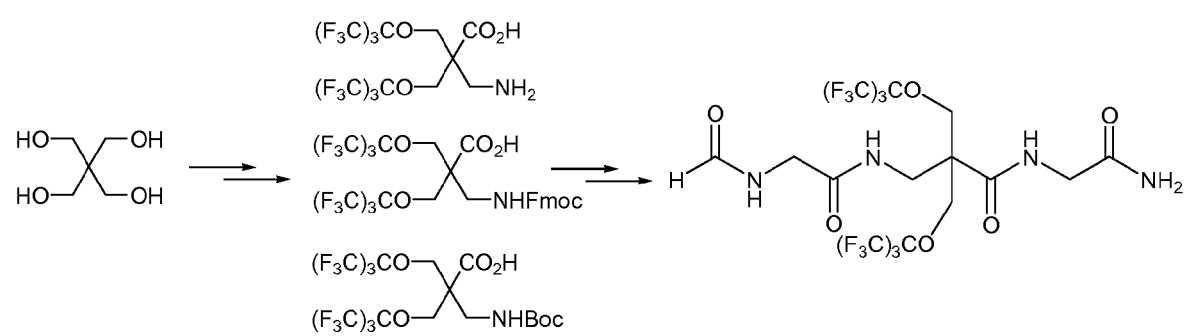
FIG. 5 shows a summary of the synthesis of exemplary highly fluorinated β-amino acids and incorporation into a peptide.

The hydrophobicity of βFa was evaluated in the context of tripeptide 4, with tripeptide 5 serving as a reference point. To this end, the reversed-phase chromatography method developed by Hodges and coworkers, who determined the relative hydrophobicity of 23 amino acids [Kovacs, J. M.; Mant, C. T.; Hodges, R. S. *Biopolymers,* 2006, 84, 283-297.], was used. FIG. 4 shows the chromatogram of the con-injection of the two tripeptides. Tripeptide 4 is much more retentive than tripeptide 5 in reversed-phase chromatography, indicating that βFa is much more hydrophobic than Trp, the most hydrophobic natural amino acid.

The 1-octanol/water partition coefficients ($P_{oct}$) of the two tripeptides were evaluated. For 5 (formyl-Gly-Trp-Gly-amide), $P_{oct}=1/9$, as determined by analytical HPLC at 280 nm (Trp signal) of the 1-octanol and aqueous phases. As for 4 (formyl-Gly-βFa-Gly-amide), after equilibration, its existence in water can be detected by neither analytical HPLC nor by $^{19}$F NMR, while its existence in 1-octanol can be readily detected by both analytical HPLC and $^{19}$F NMR. Hence, for 4, $P_{oct} \gg 10$.

Note that results of the hydrophobicity measurement and the 1-octanol/water partition coefficient measurement are entirely consistent with each other, both showing that, in the context of a peptide, βFa is very hydrophobic and strongly prefers organic over aqueous phase—thereby indicating suitability as a membrane permeability enhancer.

J. KITS

Disclosed herein are kits that are drawn to compounds and/or reagents that can be used in practicing the methods disclosed herein. The kits can include any reagent or combination of reagents discussed herein or that would be understood to be required or beneficial in the practice of the disclosed methods. For example, the kits could include reagents to perform complexation reactions discussed in certain embodiments of the methods, as well as buffers and solvents required to use the reagents as intended.

K. COMPOSITIONS WITH SIMILAR FUNCTIONS

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

L. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Synthesis of [5-Hydroxymethyl-2-(4-Methoxy-Phenyl)-[1,3]Dioxin-5-Yl]-Methanol, 7

Pentaerythritol (136.2 g, 1.0 mol) was dissolved in water (1000 mL) with heating. After the hot solution was cooled to room temperature, stirring was started and concentrated hydrochloric acid (5 mL) was added, followed by p-anisaldehyde (13.5 mL, 111.2 mmol). When the precipitate of mono-p-methylbenzilidene-pentaerythritol started forming, dropwise addition of p-anisaldehyde (115.0 mL, 947.1 mmol) was begun. After the addition of p-anisaldehyde was complete (2 hours), the mixture was stirred for additional 2 hours. The precipitate was collected and washed with diluted sodium carbonate aqueous solution and ethyl ether. The solid was dried over phosphorus pentoxide to give 7 as a white solid (222.7 g, 87%). $^{1}$H NMR (400 MHz, Acetone-d$_6$) δ 3.46 (s, 2H), 3.79 (s, 4H), 3.84 (s, 2H), 3.92 (s, 3H), 5.36 (s, 1H), 6.89-6.91 (m, 2H), 7.37-7.39 (m, 2H).

2. Synthesis of 2-(4-Methoxy-Phenyl)-5,5-Bis-(2,2,2-Trifluoro-1,1-Bis-Trifluoromethyl-Ethoxymethyl)-[1,3]Dioxane, 8

To a stirred mixture of compound 7 (24.4 g, 96.1 mmol), triphenylphosphine (75.5 g, 288.5 mmol) and 4 Å molecular sieve (20.0 g) in tetrahydrofuran (500 mL) at 0° C. was added dropwise diethylazodicarboxylate (50.2 g, 288.2 mmol). After the addition, the reaction mixture was allowed to warm to room temperature and stirred for an additional 20 minutes. Then, perfluoro-tert-butanol (68.0 g, 288.0 mmol) was added in one portion and the resulting mixture was stirred at 45° C. for 30 hours in a sealed vessel. The mixture was evaporated to dryness and the residue was dissolved in ethyl ether (600 mL). After the mixture was filtered through a pad of Celite, the filtrate was washed with brine (300 mL), dried over sodium sulfate and concentrated in vacuo. The residue was then purified by flash column chromatography on silica gel (n-hexane/ethyl acetate=20/1) to give 8 as a solid (65.1 g, 98%). mp. 89-90° C.; $^{1}$H NMR (400 MHz, CDCl$_3$) δ 3.78 (s, 1H), 3.80 (s, 4H), 3.89 (s, 2H), 4.13 (s, 1H), 4.16 (s, 1H), 4.49 (s, 2H), 5.39 (s, 1H), 6.88-6.92 (m, 2H), 7.33-7.37 (m, 2H); $^{19}$F NMR (376 MHz, CDCl$_3$) δ −73.42 (s); $^{13}$C NMR (100.7 MHz, CDCl$_3$) δ 39.2, 55.3, 66.2, 67.7, 68.7, 102.4, 113.8, 120.1 (q, J=292.6 Hz), 120.3 (q, J=292.6 Hz), 127.3, 129.9, 160.3; MS (CI) m/z 691 (M$^+$+1, 100), 690 (M$^+$, 17), 583 (22); HRMS (CI) Calcd for C$_{21}$H$_{17}$F$_{18}$O$_5$: 691.0787, Found: 691.0792.

3. Synthesis of 2,2-Bis-(2,2,2-Trifluoro-1,1-Bis-Trifluoromethyl-Ethoxymethyl)-Propane-1,3-Diol, 9

To a stirred mixture of compound 8 (33.1 g, 48.0 mmol) and anisole (20.7 g, 192.0 mmol) in dichloromethane (200 mL) at 0° C. was slowly added powdered aluminum chloride anhydrous (19.5 g, 144.0 mmol). After the addition, the reaction mixture was allowed to warm to room temperature and stirred for additional 30 minutes. The reaction mixture was quenched by slowly addition of 1N HCl (100 mL) and the resulted mixture was extracted with ether (100 mL, 3 times). The combined organic layer was concentrated in vacuo and the residue was purified by flash column chromatography on silica gel (n-hexane/ethyl acetate=8/1) to give compound 9 as a clear oil (27.4 g, 99%). $^{1}$H NMR (400 MHz, CD$_3$OD) δ 3.63 (s, 4H), 4.14 (s, 4H); $^{19}$F NMR (376 MHz, CD$_3$OD) δ −71.14 (s); $^{13}$C NMR (100.7 MHz, CD$_3$OD) δ 47.8, 60.4, 69.1, 80.9 (m), 121.8 (q, J=292.6 Hz); MS (CI) m/z 573 (M$^+$+1, 100); HRMS (CI) Calcd for C$_{13}$H$_{11}$F$_{18}$O$_4$: 573.0374, Found: 573.0374.

4. Synthesis of 5,5-Bis-(2,2,2-Trifluoro-1,1-Bis-Trifluoromethyl-Ethoxymethyl)-1,3,2-Dioxathiinane 2,2-Dioxide, 10

To a stirred solution of compound 9 (22.9 g, 40.0 mmol) and triethyl amine (16.2 g, 160.0 mmol) in dichloromethane (100 mL) and ethyl ether (100 mL) at room temperature was added dropwise a solution of thionyl chloride (9.52 g, 80.0 mmol, in 10 mL of dichloromethane). The resulting mixture was stirred for an additional 20 minutes and quenched with cold water (100 mL). The layers were separated and the aqueous layer was extracted with ether (100 mL, three times). The combined organic layer was dried over magnesium sulfate and concentrated in vacuo. The residue was purified by column chromatography on silica gel to give the cyclic sulfite intermediate (24.7 g). The cyclic sulfite (24.7 g, 40 mmol) was then dissolved with stirring in acetonitrile (50 mL), carbon tetrachloride (50 mL), and water (75 mL) at 0° C. Ruthenium trichloride (500 mg) was added to the mixture, followed by sodium periodate (17.1 g, 80.0 mmol). The reaction mixture was then stirred at room for 1 hour. The reaction was quenched with ether (200 mL) and saturated sodium bicarbonate solution (100 mL). The layers were separated and the aqueous lay was extracted with ether (100 mL, three times). The combined organic layer was dried over magnesium sulfate and concentrated in vacuo. The residue was purified by flash column chromatography on silica gel (n-hexane/ethyl acetate=10/1) to give the cyclic sulfate 10 as a solid (21.2 g, 84%). mp. 90-91° C.; $^1$H NMR (400 MHz, CDCl$_3$) δ 4.24 (s, 4H), 4.63 (s, 4H); $^{19}$F NMR (376 MHz, CDCl$_3$) δ –72.91 (s); $^{13}$C NMR (100.7 MHz, CDCl$_3$) δ 39.8, 64.9, 73.0, 80.1 (m), 120.2 (q, J=292.6 Hz); MS (CI) m/z 635 (M$^+$+1, 100); HRMS (CI) Calcd for C$_{13}$H$_9$F$_{18}$O$_6$S: 634.9832, Found: 634.9843.

5. Synthesis of 2-Azidomethyl-3-(2,2,2-Trifluoro-1, 1-Bis-Trifluoromethyl-Ethoxy)-2-(2,2,2-Trifluoro-1, 1-Bis-Trifluoromethyl-Ethoxymethyl)- Propan-1-Ol, 11

Sodium azide (4.4 g, 66.9 mmol) was added to a stirred solution of compound 10 (21.2 g, 33.4 mmol) in dimethylformaldehyde (120 mL). The reaction mixture was stirred at 60° C. for 4 hours. The solvent was removed under vacuo and the residue was dissolved in tetrahydrofuran (120 mL). Sulfuric acid (0.87 mL) and water (0.32 mL) were added to the stirred tetrahydrofuran solution and the resulting mixture was stirred at room temperature for an additional hour. After removal the solvent, the residue was redissolved in dichloromethane (200 mL) and extracted with perfluorohexane (100 mL 4 times). The combined extraction was washed with dichloromethane (10 mL) and concentrated under vacuo to give the pure azide 11 as a clear oil (19.3 g, 97%). $^1$H NMR (400 MHz, CDCl$_3$) δ 3.47 (s, 2H), 3.63 (s, 2H), 4.02 (s, 4H); $^{19}$F NMR (376 MHz, CDCl$_3$) δ –73.21 (s); $^{13}$C NMR (100.7 MHz, CDCl$_3$) δ 45.8, 49.8, 60.2, 66.8, 79.6 (m), 120.2 (q, J=293.3 Hz); MS (CI) m/z 598 (M$^+$+1, 72), 570 (100); HRMS (CI) Calcd for C$_{13}$H$_{10}$F$_{18}$N$_3$O$_3$: 598.0435, Found: 598.0418.

6. Synthesis of 2-Azidomethyl-3-(2,2,2-Trifluoro-1, 1-Bis-Trifluoromethyl-Ethoxy)-2-(2,2,2-Trifluoro-1, 1-Bis-Trifluoromethyl-Ethoxymethyl)-Propionic Acid, 12

To a stirred solution of alcohol 11 (19.0 g, 31.8 mmol) at 0° C. was added dropwise a solution of Jones reagent (2.7 N, 31 mL). After addition, the reaction mixture was stirred at room temperature for 1 hour and 2-propanol (10 mL) was slowly added. The solvent was removed under vacuo and the residue was dissolved in ether. Washing the ether solution with water, separation the layers and the aqueous lay was extracted with ether. The combined organic lay was dried over magnesium sulfate and concentrated in vacuo. The residue was purified by flash column chromatography on silica gel (n-hexane/ethyl acetate=1/1) to give the acid 12 as a solid (18.5 g, 95%). mp. 97-98° C.; $^1$H NMR (400 MHz, CD$_3$OD) δ 3.62 (s, 2H), 4.25 (d, J=8.8 Hz, 2H), 4.33 (d, J=8.4 Hz, 2H); $^{19}$F NMR (376 MHz, CD$_3$OD) δ –71.16 (s); $^{13}$C NMR (100.7 MHz, CD$_3$OD) δ 50.9, 53.6, 67.5, 81.2 (m), 121.6 (q, J=292.6 Hz), 171.9; MS (CI) m/z 612 (M$^+$+1, 100), 584 (80); HRMS (CI) Calcd for C$_{13}$H$_8$F$_{18}$N$_3$O$_4$: 612.0227, Found: 612.0204.

7. Synthesis of 2-Aminomethyl-3-(2,2,2-Trifluoro-1, 1-Bis-Trifluoromethyl-Ethoxy)-2-(2,2,2-Trifluoro-1, 1-Bis-Trifluoromethyl-Ethoxymethyl)-Propionic Acid, 1

A mixture of Palladium on carbon (2.5 g) in methanol (200 mL) was degassed for 2 minutes and stirred under a hydrogen atmosphere for 30 minutes. A solution of acid 12 (10.7 g, 17.5 mmol) in methanol (10 mL) was then added and the resulting mixture was stirred at room temperature under a hydrogen atmosphere for additional 30 hours. After removal solvent, the resulting residue was purified by flash column chromatography on silica gel (methanol/dichloromethane=10/1) to give the amino acid 1 as a solid (10.1 g, 98%). mp. 182-184° C.; $^1$H NMR (400 MHz, CD$_3$OD) δ 2.99 (s, 2H), 4.22 (d, J=9.2 Hz, 2H), 4.49 (d, J=8.4 Hz, 2H); $^{19}$F NMR (376 MHz, CD$_3$OD) δ –71.00 (s); $^{13}$C NMR (100.7 MHz, CD$_3$OD) δ 41.7, 52.1, 69.9, 80.9 (m), 121.7 (q, J=292.6 Hz), 175.0; MS (CI) m/z 586 (M$^+$+1, 100); HRMS (CI) Calcd for C$_{13}$H$_{10}$F$_{18}$NO$_4$: 586.0322, Found: 586.0285.

8. Synthesis of 2-[(9H-Fluoren-9-Ylmethoxycarbonylamino)-Methyl]-3-(2,2,2-Trifluoro-1,1-Bis-Trifluoromethyl-Ethoxy)-2-(2,2,2-Trifluoro-1,1-Bis-Trifluoromethyl-Ethoxymethyl)-Propionic Acid, 2

To a stirred solution of amino acid 1 (10.1 g, 17.2 mmol) in tetrahydrofuran (100 mL) and water (100 mL) was added sodium carbonate (4.6 g, 42.9 mmol). After all the sodium carbonate was dissolved, the resulting mixture was cooled to 0° C. and 9-fluorenylmethyl chloroformate (6.7 g, 25.9 mol) was added in three portions. The resulted reaction mixture was stirred at room temperature overnight. The solvent was removed under vacuo and the residue was purified by flash column chromatography on silica gel (n-hexane/ethyl acetate=5/1) to give the acid 2 as a white solid (13.3 g, 96%). mp. 104-105° C.; $^1$H NMR (400 MHz, CD$_3$OD) δ 3.45 (s, 2H), 4.16 (m), 4.27 (m, 4H), 4.46 (d, J=8.8 Hz, 2H) 7.26 (t, J=7.2 Hz, 2H), 7.35 (t, J=7.2 Hz, 2H), 7.60 (d, J=7.6 Hz, 2H), 7.74 (d, J=7.2 Hz, 2H); $^{19}$F NMR (376 MHz, CD$_3$OD) δ –71.00 (s); $^{13}$C NMR (100.7 MHz, CD$_3$OD) δ 36.9, 42.8, 53.7, 68.2, 69.0, 80.9 (m), 120.9, 121.7 (q, J=292.6 Hz), 126.2, 128.1, 128.8, 142.6, 145.2, 158.8, 174.4; MS (CI) m/z 808 (M$^+$+1, 100); HRMS (CI) Calcd for C$_{28}$H$_{20}$F$_{18}$NO$_6$: 808.1003, Found: 808.1010.

9. Synthesis of 3-Tert-Butoxycarbonylamino-2,2-Bis-(2,2,2-Trifluoro-1,1-Bis-Trifluoromethyl-Ethoxymethyl)-Propionic Acid, 3

A mixture of Palladium on carbon (200 mg) in methanol (20 mL) was degassed for 2 minutes and stirred under hydrogen atmosphere for 30 minutes. A solution of acid 12 (1.2 g, 2.0 mmol) and di-tert-butyl dicarbonate (872 mg, 4.0 mmol) in methanol (5 mL) was then added and the resulting mixture was stirred at room temperature under an atmosphere of hydrogen gas for 30 hours. After removal solvent, the resulting residue was purified by flash column chromatography on silica gel (n-hexane/ethyl acetate=5/1) to give the amino acid 3 as a solid (1.32 g, 96%). mp. 128-130° C.; $^1$H NMR (400 MHz, CD$_3$OD) δ 1.36 (s, 9H), 3.31 (s, 2H), 4.17 (d, J=8.0 Hz, 2H), 4.39 (d, J=8.0 Hz, 2H); $^{19}$F NMR (376 MHz, CD$_3$OD) δ

−71.01 (s); $^{13}$C NMR (100.7 MHz, CD$_3$OD) δ 28.8, 42.8, 54.1, 69.6, 80.7, 81.1 (m), 121.9 (q, J=293.3 Hz), 158.1, 177.2; MS (CI) m/z 686 (M$^+$+1, 10), 644 (100); HRMS (CI) Calcd for C$_{18}$H$_{18}$F$_{18}$NO$_6$: 686.0847, Found: 686.0815.

10. Synthesis of Formyl-Gly-βFa-Gly-Amide, 4

The peptide was synthesized using standard Fmoc chemistry on Rink Amide MBHA resin (which gives C-terminal amide). TBTU and HOBt were employed as coupling reagents. The coupling time for each residue is 1 hour with a five-fold amount of Fmoc-amino acid, except for βFa (which is 8 hours with a two-fold βFa). The tripeptide was cleaved from the resin using 90% trifluoroacetic acid with 2.5% each of tri-isopropyl silane, water, anisole, and dichloromethane. The cleavage product was concentrated under vacuum and purified using normal phase chromatography using a TSK-GEL Amide-80 column (300×21.5 mm I.D.; 10-μm particle size) with methanol and acetonitrile as the eluents (2% MeOH/min, starting from 0% MeOH, at a flow rate of 5 mL/min, at 25° C.). $^1$H NMR (400 MHz, CD$_3$OD) δ 3.50 (s, 2H), 3.80 (s, 2H), 3.81 (s, 2H), 4.19 (d, J=9.2 Hz, 2H), 4.29 (d, J=9.2 Hz, 2H), 8.03 (s, 1H); $^{19}$F NMR (376 MHz, CD$_3$OD) δ −70.97 (s); MS (MALDI-TOF) m/z 749 (M+Na)$^+$.

11. Synthesis of Formyl-Gly-Trp-Gly-Amide, 5

The peptide was synthesized and cleaved by the same method as for compound 4. The cleavage product was concentrated under vacuum and precipitated with cold ether, and the precipitate was purified by reversed-phase chromatography using a Zorbax 300SB-C18 column (250×21.2 mm I.D.; 7-μm particle size) with water and acetonitrile at pH 2 (2% acetonitrile/min, starting from 0% acetonitrile, at a flow rate of 5 mL/min, at 25° C.). $^1$H NMR (400 MHz, CD$_3$OD) δ 3.54-3.84 (m, 4H), 4.46-4.50 (m, 1H), 6.91-7.03 (m, 3H), 7.23 (d, J=8.4 Hz, 1H), 7.48 (d, J=7.6 Hz, 1H), 7.99 (s, 1H); MS (MALDI-TOF) m/z 368 (M+Na)$^+$.

12. Determination Partition Coefficients of Peptides 4 and 5

To 20 mg of peptide 4 or 5 were added 2 mL of water and 2 mL of 1-octanol. The resulting mixture was shaken with a mixer for 10 min. After the aqueous and the organic phases were fully separated, 50 μL of solution was taken out from each phase for HPLC analysis. To a mixture of 200 μL aqueous solution and 200 μL 1-octanol solution were added 1.8 mL of water and 1.8 mL of 1-octanol. The resulting mixture was shaken with a mixer for 10 min. After the phases were fully separated, 50 μL of solution was taken out from each phase for reversed-phases HPLC analysis. Partition profiles of 4 and 5 at these two different concentrations are comparable, according to HPLC analysis. Formyl-Gly-βFa-Gly-amide 4 can only be detected in the 1-octanol phase. Formyl-Gly-Trp-Gly-amide 5 can be detected in both the 1-octanol and the aqueous phases and the partition coefficient P$_{oct}$ is 1/9 (1-octanol/water), based on the ratio of the areas of HPLC peaks monitored at 280 nm. Solutions for the tripeptide formyl-Gly-βFa-Gly-amide 4 were also taken for $^{19}$F NMR analysis, and $^{19}$F NMR signal was detected only in the 1-octanol phase.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the structure:

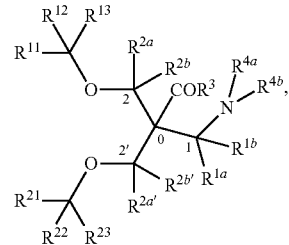

wherein R$^{1a}$ and R$^{1b}$ are independently H, alkyl, F, or fluoroalkyl;

wherein R$^{2a}$, R$^{2b}$, R$^{2a'}$, and R$^{2b'}$ are independently H, alkyl, F, fluoroalkyl, aryl, or alkenyl;

wherein R$^3$ is OH, alkoxyl, NH$_2$, alkylamino, or dialkylamino;

wherein R$^{4a}$ and R$^{4b}$ are independently H, alkyl, acyl, or alkyloxycarbonyl;

wherein R$_{11}$, R$_{12}$, R$_{13}$, R$_{21}$, R$_{22}$, and R$_{23}$ are independently H, alkyl, F, or fluoroalkyl; and wherein C0, C1, C2, and C2' are independently chiral or achiral.

2. The compound of claim 1, wherein R$^{11}$=R$^{12}$=R$^{13}$.

3. The compound of claim 1, wherein R$^{21}$=R$^{22}$=R$^{23}$.

4. The compound of claim 1, wherein R$^{11}$, R$^{12}$, R$^{13}$, R$^{21}$, R$^{22}$, and R$^{23}$ are fluoroalkyl.

5. The compound of claim 1, wherein R$^{1a}$, R$^{1b}$, R$^{2a}$, R$^{2b}$, R$^{2a'}$, and R$^{2b'}$ are H; wherein C1, C2, and C2' are achiral; and wherein the compound has the structure:

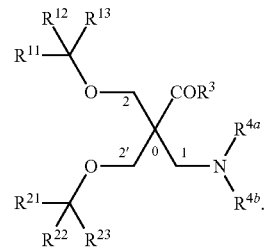

6. The compound of claim 1, wherein R$^{11}$=R$^{12}$=R$^{13}$=R$^{21}$=R$^{22}$=R$^{23}$ and wherein C0 is achiral.

7. The compound of claim 1, wherein R$^{11}$=R$^{12}$=R$^{13}$≠R$^{21}$=R$^{22}$=R$^{23}$ and wherein C0 is chiral.

8. The compound of claim 5, wherein R$^{11}$, R$^{12}$, R$^{13}$, R$^{21}$, R$^{22}$, and R$^{23}$ are CF$_3$;

wherein R$^{4a}$ is H; wherein R$^{4b}$ is H or Fmoc; and wherein the compound has the structure:

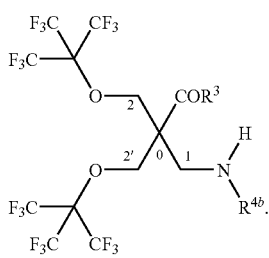

9. A process for making a fluorinated β-amino acid comprising the steps of:
a) providing a diol having the structure:

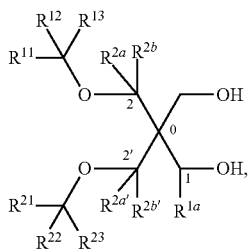

wherein $R^{1a}$ and $R^{1b}$ are independently H, alkyl, F, or fluoroalkyl;

wherein $R^{2a}$, $R^{2b}$, $R^{2a'}$, $R^{2b'}$, $R^{11}$, $R^{12}$, $R^{13}$, $R^{21}$, $R^{22}$, and $R^{23}$ are independently H, alkyl, F, fluoroalkyl, aryl, or alkenyl;

wherein $R^{11}$, $R^{12}$, $R^{13}$, $R^{21}$, $R^{22}$, and $R^{23}$ are independently F or fluoroalkyl; and wherein C0, C1, C2, and C2' are independently chiral or achiral;

b) treating the diol with a thionyl halide with oxidative workup;

c) reacting the product of step (b) with an azide salt to yield an azido group;

d) oxidizing the product of step (c) to yield a carboxyl group; and e) reducing the azido group to yield an amino group.

10. The process of claim 9, wherein $R^{1a}$, $R^{2a}$, $R^{2b}$, $R^{2a'}$, and $R^{2b'}$ are H; wherein $R^{11}$, $R^{12}$, $R^{13}$, $R^{21}$, $R^{22}$, and $R^{23}$ are $CF_3$; and wherein the compound has the structure:

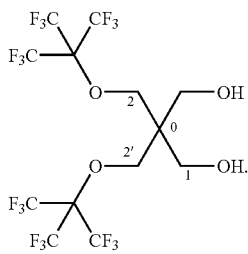

11. The process of claim 9, wherein the product of step (b) has the structure:

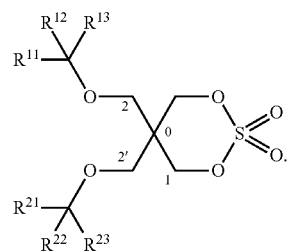

12. The process of claim 9, wherein the providing step comprises the steps of:
a) providing a tetra-ol; and
b) protecting two hydroxyl groups of the tetra-ol.

13. The process of claim 12, wherein the protecting step is reaction with a carbonyl compound to form a cyclic ketal or cyclic acetal.

14. The product produced by a process for making a fluorinated β-amino acid comprising the steps of:
a) providing a diol having the structure:

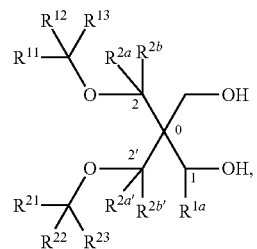

wherein $R^{1a}$ and $R^{1b}$ are independently H, alkyl, F, or fluoroalkyl; wherein $R^{2a}$, $R^{2b}$, $R^{2a'}$, $R^{2b'}$, $R^{11}$, $R^{12}$, $R^{13}$, $R^{21}$, $R^{22}$, and $R^{23}$ are independently H, alkyl, F, fluoroalkyl, aryl, or alkenyl;

wherein $R^{11}$, $R^{12}$, $R^{13}$, $R^{21}$, $R^{22}$, and $R^{23}$ are independently F or fluoroalkyl; and wherein C0, C1, C2, and C2' are independently chiral or achiral;

b) treating the diol with a thionyl halide with oxidative workup;

c) reacting the product of step (b) with an azide salt to yield an azido group;

d) oxidizing the product of step (c) to yield a carboxyl group; and e) reducing the azido group to yield an amino group.

15. A peptide comprising at least one residue of a compound having the structure:

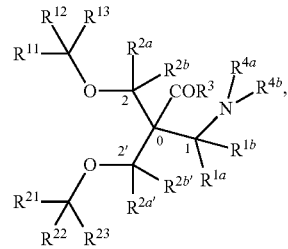

wherein $R^{1a}$ and $R^{1b}$ are independently H, alkyl, F, or fluoroalkyl;

wherein $R^{2a}$, $R^{2b}$, $R^{2a'}$, and $R^{2b'}$ are independently H, alkyl, F, fluoroalkyl, aryl, or alkenyl;
wherein $R^3$ is OH, alkoxyl, $NH_2$, alkylamino, or dialkylamino;
wherein $R^{4a}$ and $R^{4b}$ are independently H, alkyl, acyl, or alkyloxycarbonyl;
wherein $R_{11}$, $R_{12}$, $R_{13}$, $R_{21}$, $R_{22}$, and $R_{23}$ are independently H, alkyl, F, or fluoroalkyl; and
wherein C0, C1, C2, and C2' are independently chiral or achiral, or
at least one residue of the product of a process for making a fluorinated β-amino acid comprising the steps of:
a) providing a diol having the structure:

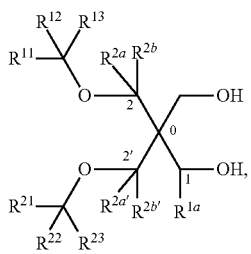

wherein $R^{1a}$ and $R^{1b}$ are independently H, alkyl, F, or fluoroalkyl; wherein $R^{2a}$, $R^{2b}$, $R^{2a'}$, $R^{2b'}$, $R^{11}$, $R^{12}$, $R^{13}$, $R^{21}$, $R^{22}$, and $R^{23}$ are independently H, alkyl, F, fluoroalkyl, aryl, or alkenyl;
wherein $R^{11}$, $R^{12}$, $R^{13}$, $R^{21}$, $R^{22}$, and $R^{23}$ are independently F or fluoroalkyl; and
wherein C0, C1, C2, and C2' are independently chiral or achiral;
b) treating the diol with a thionyl halide with oxidative workup;
c) reacting the product of step (b) with an azide salt to yield an azido group;
d) oxidizing the product of step (c) to yield a carboxyl group; and
e) reducing the azido group to yield an amino group.

16. The peptide of claim 15, having the structure:

Z-βFa-Cys-M-D-Trp-Lys-A-Cys-A-X, wherein βFa comprises a residue of a compound having the structure:

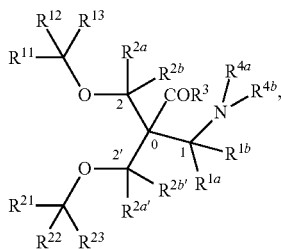

wherein $R^{1a}$ and $R^{1b}$ are independently H, alkyl, F, or fluoroalkyl;
wherein $R^{2a}$, $R^{2b}$, $R^{2a'}$, and $R^{2b'}$ are independently H, alkyl, F, fluoroalkyl, aryl, or alkenyl;
wherein $R^3$ is OH, alkoxyl, $NH_2$, alkylamino, or dialkylamino;
wherein $R^{4a}$ and $R^{4b}$ are independently H, alkyl, acyl, or alkyloxycarbonyl;

wherein $R_{11}$, $R_{12}$, $R_{13}$, $R_{21}$, $R_{22}$, and $R_{23}$ are independently H, alkyl, F, or fluoroalkyl; and
wherein C0, C1, C2, and C2' are independently chiral or achiral, or
a residue of the product of a process for making a fluorinated β-amino acid comprising the steps of:
a) providing a diol having the structure:

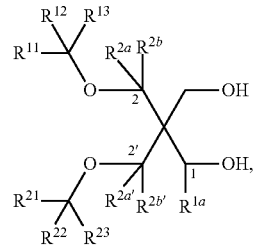

wherein $R^{1a}$ and $R^{1b}$ are independently H, alkyl, F, or fluoroalkyl;
wherein $R^{2a}$, $R^{2b}$, $R^{2a'}$, $R^{2b'}$, $R^{11}$, $R^{12}$, $R^{13}$, $R^{21}$, $R^{22}$, and $R^{23}$ are independently H, alkyl, F, fluoroalkyl, aryl, or alkenyl;
wherein $R^{11}$, $R^{12}$, $R^{13}$, $R^{21}$, $R^{22}$, and $R^{23}$ are independently F or fluoroalkyl; and
wherein C0, C1, C2, and C2' are independently chiral or achiral;
b) treating the diol with a thionyl halide with oxidative workup;
c) reacting the product of step (b) with an azide salt to yield an azido group;
d) oxidizing the product of step (c) to yield a carboxyl group; and
e) reducing the azido group to yield an amino group;
wherein each A independently comprises a residue of threonine or a residue of 4,4,4-trifluorothreonine;
wherein M comprises Phe or Tyr or a derivatives thereof;
wherein X comprises a terminal end group selected from carboxyl, ester, amide, and alcohol; and
wherein Z comprises a terminal end group selected from amino, formyl, acetyl, and succinyl.

17. The peptide of claim 16, wherein the cysteine residues are linked by a disulfide bond.

18. The peptide of claim 16, having the structure:

Z-βFa-Cys-M-D-Trp-Lys-A-Cys-tfT-X, wherein each A independently comprises a residue of threonine or a residue of 4,4,4-trifluorothreonine; and
wherein tfT comprises a residue of 4,4,4-trifluorothreonine.

19. The peptide of claim 16, having the structure:

Z-βFa-Cys-M-D-Trp-Lys-tfT-Cys-A-X, wherein each A independently comprises a residue of threonine or a residue of 4,4,4-trifluorothreonine; and
wherein tfT comprises a residue of 4,4,4-trifluorothreonine.

20. The peptide of claim 16, having the structure:

Z-βFa-Cys-M-D-Trp-Lys-tfT-Cys-tfT-X, wherein tfT comprises a residue of 4,4,4-trifluorothreonine.

* * * * *